United States Patent [19]

Guala

[11] Patent Number: 4,865,988
[45] Date of Patent: Sep. 12, 1989

[54] MICROBIOLOGICAL CULTURE DEVICE

[76] Inventor: Piergiacomo Guala, Via Trotti, 21, 15100 Alessandria, Italy

[21] Appl. No.: 195,110

[22] Filed: May 16, 1988

[30] Foreign Application Priority Data

Jun. 25, 1987 [IT] Italy ............................... 21047 A/87

[51] Int. Cl.⁴ ............................................... C12M 1/24
[52] U.S. Cl. .................................... 435/296; 435/285; 435/299; 206/569; 215/10
[58] Field of Search ............... 435/285, 296, 299, 300; 206/569; 215/10; 220/339; 422/61, 102

[56] References Cited

U.S. PATENT DOCUMENTS 3,651,926  3/1972  Elfast .................................. 435/296
3,741,877  6/1973  Shaufus et al. ....................... 435/299
4,483,450  11/1984  Sanchez ................................. 215/10

FOREIGN PATENT DOCUMENTS 51-7745  3/1976  Japan .................................... 435/296

Primary Examiner—Noah P. Kamen
Attorney, Agent, or Firm—Notaro & Michalos

[57] ABSTRACT

A microbiological culture device which affords improved lapping over a surface to be tested comprises an elongated plate carrying a culture medium, a tubular case for the plate, and a stopper for the case made fast with one end of the plate and providing a handgrip for holding the plate, as well as an elastically deformable bridge formed on the plate the one end.

6 Claims, 1 Drawing Sheet

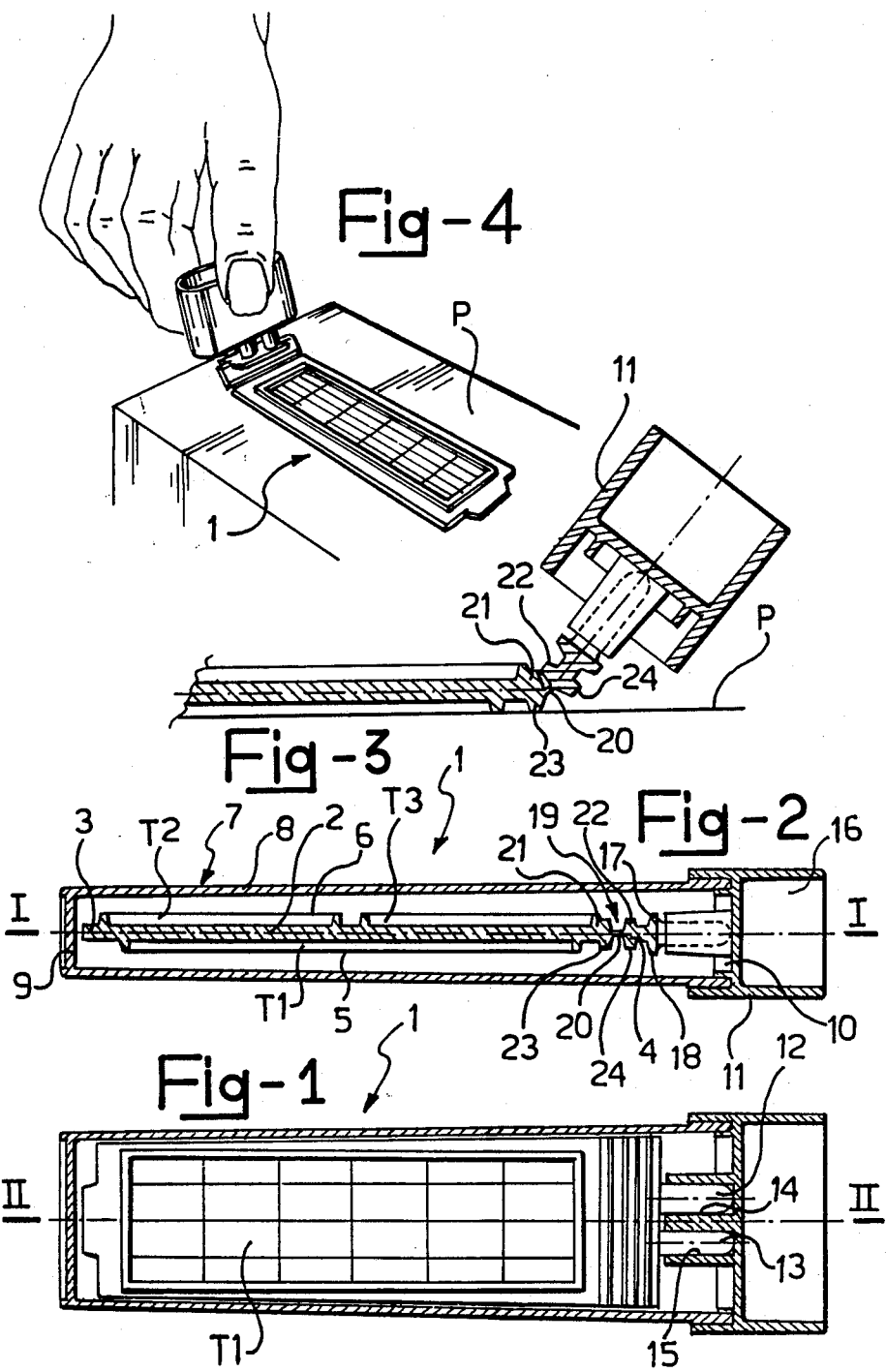

MICROBIOLOGICAL CULTURE DEVICE

FIELD AND BACKGROUND OF THE INVENTION

This invention relates to a microbiological culture device of a type which comprises an elongate plate carrying a culture, medium, a tubular case for said plate, and a stopper made fast with one end of said plate and closing said case.

As is known, there exists a need to periodically check the sanitary conditions of such public establishments as the kitchens of restaurants, canteens, and the like.

Such inspections are carried out, e.g. by health officers, with the aid of microbiological culture devices by bringing a small plate or slide which carries the culture medium into lapping engagement with the kitchen work surfaces, such as tables, shelves of various description, and so forth, for the purpose of picking up any bacteria therefrom.

Conventional devices employed for the purpose, while being extensively used and in many ways successfully, still have some shortcomings.

In particular, prior devices only enable lapping of the work surfaces limited to the edge regions thereof. Where the central region of a surface is to be lapped, then the plate must be taken apart from the stopper and manipulated in this detached condition, with the risk of coming into contact with the culture medium.

Devices have been proposed wherein the plates or slides enjoy a degree of flexibility, thereby they can be made to adhere, to some extent, closely against a surface to be lapped. However, it is found with that approach that the culture medium can easily separate from the plate.

SUMMARY OF THE INVENTION

The problems that underlies this invention is to provide a device of the kind specified above, which has such constructional and operational features as to overcome the above-noted shortcomings affecting the prior art.

This problem is solved by a device as indicated being characterized in that it comprises a hinge formed on said plate at the end thereof made fast with the stopper.

Advantageously, said hinge is an elastically deformable bridge formed integrally with the plate.

Further features and the advantages of the device according to this invention will become apparent from the following detailed description of a preferred embodiment thereof, to be taken by way of illustration and not of limitation in conjunction with the accompanying drawings.

BRIEF DESCRIPTION OF THE DRAWINGS

In the drawings:

FIG. 1 is a sectional view taken through a device according to the invention along the line I—I of FIG. 2;

FIG. 2 is a sectional view through the device shown in FIG. 1, taken along the line II—II;

FIG. 3 is a sectional detail view of the device of FIG. 1 at a different stage of its operation; and FIG. 4 is a perspective detail view of the device shown in FIG. 1.

DESCRIPTION OF THE PREFERRED EMBODIMENT

With reference to the drawing views, the numeral 1 designates generally a microbiological culture device according to the invention. The device 1 comprises a small elongated plate, or slide 2 of substantially rectangular shape, having two opposed ends 3 and 4, and two opposed faces 5 and 6.

Zones are defined on the faces 5 and 6, one on the face 5 and two on the face 6, which are formed with suitable corrugations to accommodate respective culture media T1, T2, and T3.

The device 1 further comprises a tubular case 7 having a skirt 8, bottom 9, and opening 10.

The plate 2 fits inside the case 7 in a guided sliding fashion, with the end 3 next to the bottom 9 and the end 4 substantially level with the opening 10.

Indicated at 11 is a stopper which is a press-fit over the skirt 8 to close the case opening 10, and is fast with the end 4 of the plate, thereby providing a handgrip for the plate.

In particular, in continuation of the plate end 4, there are integrally formed two plugs 12 and 13, preferably with different diameters, which fit snugly into two corresponding sockets 14 and 15 formed in the stopper 11 on the case side thereof. At its opposed end, the stopper 11 has an impression 16 sized to accommodate a bottom 9 of another device identical with the device 1 in a predetermined snug fit relationship so as to provide a stack of the devices.

At the bottoms of the plugs 12 and 13 there are formed two small wings 17 and 18, one extending of each face of the plate, to provide a grip and facilitate forced insertion of the plugs into their respective sockets.

Formed on the device 1 of this invention, at the end 4 of the plate, is a hinge, indicated at 19, around which the plate is swung in an angularly displaceable manner.

Advantageously, the hinge 19 is embodied by a small bridge 20 formed integrally with the plate, which is made deformable elastically by its slender thickness dimension.

Formed on the face 6 of the plate, on opposed sides of the bridge 20, are two projections 21 and 22, and two similar projections 23 and 24 are formed on the face 5.

The projections 21 and 22, and projections 23 and 24, are sized to come into mutual abutment relationship when the plate completes a predetermined angular movement around the hinge, thereby acting as stops for said angular movement.

In the example illustrated, the maximum angle allowed for the angular movement is about 45° in either directions.

It should be noted that with such amplitudes of the angular movement, the stopper 11 is located sufficiently away from the plane defined by the face 6 or the plane defined by the face 5 of the plate.

Under such conditions, in operation of the device, the stopper can be easily grasped (see FIG. 4) for lapping over a surface P to be tested in any areas of the surface by means of the plate.

The lapping can be effected with a desired pressure of the plate 2 on the surface P to be tested. It will be sufficient, in fact, to exert an appropriate pressure on the stopper-grip for transfer to the plate via the projections 21 and 22, or 23 and 24, in mutual abutment relationship.

The main advantage of the device according to this invention is that it enables lapping over a surface at any locations thereof.

A further advantage of the invention device is that the surface lapping operation can be carried out easily at a desired pressure of the plate on the surface being tested.

Lastly, it should be noted that the device of this invention is simple construction-wise and inexpensive to manufacture, which are not neglibible advantages in the instance of an article which must be produced on a large volume basis and discarded after use.

Understandably, to a device as disclosed hereinabove, a skilled person in the art may, in order to meet specific and contingent demands, apply numerous modifications and variations, without departing from the true scope of the invention as set forth in the appended claims.

I claim:

1. A microbiological culture device comprising an elongated plate for carryng a culture medium, a tubular case having a bottom and an opening for receiving said plate, a stopper engaged with one end of said plate and closing said case when said plate is received in said case, a hinge connected between said stopper and said plate, a first projection on one side of said hinge adjacent said plate and a second projection on an opposite side of said hinge adjacent said stopper, said first and second projection extending from at least one side of said plate and engageable with each other to stop an angular displacement of said stopper with respect to said plate, around said hinge.

2. A microbiological culture device according to claim 1, wherein said stopper includes an impression sized to accomodate a bottom of the case of another device in snug fit relationship to form a stacked arrangement.

3. A microbiological culture device according to claim 1 wherein said hinge comprises an elastically deformable bridge connected between said plate and said stopper.

4. A microbiological culture device according to claim 3 including first and second projections extending from said respective plate and stopper, adjacent said hinge, on both sides of said plate.

5. A microbiological culture device according to claim 4, wherein stopper includes an impression sized to accommodate a bottom of the case of another device in snug fit relationship to form a stacked arrangement.

6. A microbiological culture device according to claim 1 including first and second projections extending from said respective plate and stopper, adjacent said hinge, on both sides of said plate.

* * * * *

UNITED STATES PATENT AND TRADEMARK OFFICE
CERTIFICATE OF CORRECTION

PATENT NO. : 4,865,988

DATED : September 12, 1989

INVENTOR(S) : Piergiacomo Guala

It is certified that error appears in the above-identified patent and that said Letters Patent is hereby corrected as shown below:

On the title page:

-[73] Assignee: STA.TE. S.p.A.
--Alessandria, Italy

Signed and Sealed this

Eighteenth Day of June, 1991

Attest:

HARRY F. MANBECK, JR.

Attesting Officer

Commissioner of Patents and Trademarks